United States Patent [19]

Chapleo et al.

[11] Patent Number: 4,818,764
[45] Date of Patent: Apr. 4, 1989

[54] IMIDAZOLINE DERIVATIVE AND METHOD OF TREATING DEPRESSION THEREWITH

[75] Inventors: Christopher Chapleo, Swanland; Peter L. Myers, Cottingham, both of England

[73] Assignee: Reckitt & Colman Products Limited, England

[21] Appl. No.: 230,195

[22] Filed: Feb. 2, 1981

[30] Foreign Application Priority Data

Feb. 4, 1980 [GB] United Kingdom ............... 8003636

[51] Int. Cl.$^4$ .................. A61K 31/415; C07D 403/00
[52] U.S. Cl. ..................................... 514/397; 548/348
[58] Field of Search .......................... 548/348; 514/397

[56] References Cited

U.S. PATENT DOCUMENTS

| | | | |
|---|---|---|---|
| 2,641,601 | 6/1953 | Goldberg et al. | 548/348 |
| 2,979,511 | 4/1961 | Krapebo et al. | 548/348 |
| 4,301,171 | 11/1981 | Kluge et al. | 548/348 |
| 4,302,469 | 11/1981 | Kluge et al. | 548/348 |
| 4,315,021 | 2/1982 | Kluge et al. | 548/348 |
| 4,352,809 | 10/1982 | Bondinell et al. | 548/348 |

FOREIGN PATENT DOCUMENTS

| | | | |
|---|---|---|---|
| 0074711 | 8/1981 | European Pat. Off. | 548/348 |
| 2903653 | 2/1979 | Fed. Rep. of Germany | 548/348 |

OTHER PUBLICATIONS

Lands, et al., Nature (1967) 214, pp. 597–598.
Ahlguist, Amer. J. Physiol., (1948) 153, pp. 586–600.
Powell & Slater, J. Pharmac. Exp. Ther., (1958) 122 pp. 480–488.
Langer, Br. J. Pharmac., (1977) 60, p. 481.
Caroon, et al., J. Med. Chem., (1982) 25, pp. 666–670.
Michel, et al., Proc. Brit. Pharm. Soc., (1981), pp. 1, 98 & 99.
Whitmore, Organic Chemistry, Van Nostrand Co, Inc., New York, 1951, p. 380.

*Primary Examiner*—Alan L. Rotman
*Assistant Examiner*—Robert C. Whittenbaugh
*Attorney, Agent, or Firm*—Bacon & Thomas

[57] ABSTRACT

2-[2-(1,4-Benzodioxanyl)]-2-imidazoline or a non-toxic salt thereof, substantially free of 2-[2-(2-methyl-1,3-benzodioxyl)]- 2-imidazoline or a non-toxic salt thereof.

2-[2-(1,4-Benzodioxanyl)]-2-imidazoline or a non-toxic salt thereof characterised in that the nuclear magnetic resonance spectrum of the compound in a protonated form exhibits multiplets in the region of $\tau 4.4$ and $\tau 5.4$.

Process for the preparation of 2-[2-(1,4-benzodioxanyl)]-2-imidazoline, pharmaceutical compositions thereof or of its salts, and their use as presynaptic $\alpha_2$-adrenoreceptor antagonists.

4 Claims, No Drawings

IMIDAZOLINE DERIVATIVE AND METHOD OF TREATING DEPRESSION THEREWITH

This invention relates to an imidazoline derivative, its non-toxic salts, a process for its preparation and pharmaceutical compositions of the derivative or its salts.

The specification of U.S. Pat. No. 2,979,511 purports to disclose the compounds of the general formula

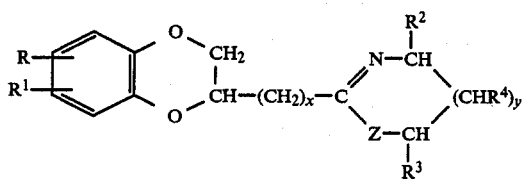

and acid-addition salts of those compounds which contain a basic nitrogen atom, wherein R and $R^1$ are the same or different and represent hydrogen, hydroxy, halogen, trifluoromethyl, nitro, lower alkyl, alkenyl or lower alkoxy; $R^2$, $R^3$ and $R^4$ are the same or different and represent hydrogen or lower alkyl; x is zero or one, y is zero or one, and Z is —NH—, or —N(lower alkyl)—. Particularly preferred are compounds wherein R, $R^1$, $R^2$, $R^3$ and $R^4$ are hydrogen, y is zero, and Z is —NH—.

The compounds are prepared by heating a compound of the general formula

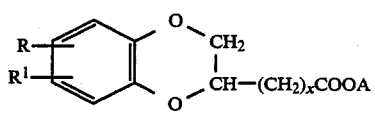

wherein R, $R^1$, and x are as hereinbefore defined, and A is hydrogen or lower alkyl (preferably methyl), with a compound of the general formula

wherein $R^2$, $R^3$, $R^4$, y and Z are as hereinbefore defined.

The specification of this U.S. patent describes the preparation in Example 1 of a compound said to be 2-[2-(1,4-benzodioxanyl)]-2-imidazoline hydrochloride, according to the above mentioned method comprising the refluxing of a mixtue of 1,4-benzodioxan-2-carboxylic acid with ethylenediamine with subsequent removal of the resultant water. In the Example the reaction mixture was worked up by fractional distillation to afford the alleged compound as the base which was then converted to the hydrochloride salt melting at about 241°–243° C. (dec.).

We have now repeated the preparation (as described below in Example 2) and established that the compound isolated in fact has the structure

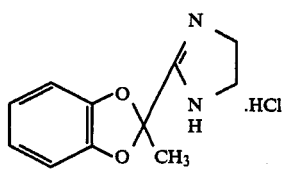

the compound being 2-[2-(2-methyl-1,3-benzodioxyl)]-2-imidazoline hydrochloride.

We have now successfully prepared 2-[2-(1,4-benzodioxanyl)]-2-imidazoline of formula IV as its hydrochloride salt.

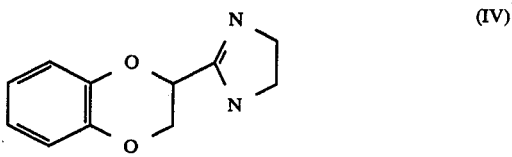

According to this invention there is provided 2-[2-(1,4-benzodioxanyl)]-2-imidazoline or a non-toxic salt thereof, substantially free of 2-[2-(2-methyl-1,3-benzodioxoyl)]-2-imidazoline or a non-toxic salt thereof.

It will be appreciated that the compound of formula IV contains an asymmetric carbon atom and it is to be understood that the invention includes both the racemic mixture and the optically active enantiomers.

In a further aspect of the invention, there is provided 2-[2-(1,4-benzodioxanyl)]-2-imidazoline or a non-toxic salt thereof characterised in that the nuclear magnetic resonance spectrum of the compound in a protonated form exhibits multiplets in the regions of $\tau 4.4$ and $\tau 5.4$.

The invention also includes pharmaceutical compositions comprising 2-[2-(1,4-benzodioxanyl)]-2-imidazoline or a non-toxic salt thereof, substantially free of 2-[2-(2-methyl-1,3-benzodioxyl-2-imidazoline or a non-toxic salt thereof, together with a pharmaceutically acceptable diluent or carrier.

Examples of non-toxic salts are those with inorganic acids such as hydrochloric acid, sulphuric or phosphoric acid; or organic acids as acetic, propionic, malonic, succinic, fumaric, tartaric, citric or cinnamic acid. A preferred salt is the hydrochloride.

The adrenoreceptors of the sympathetic nervous system have for many years been classified into two main types namely alpha ($\alpha$) and beta ($\beta$). In recent years this classification has needed to be modified since subgroups of each type have been identified making the full classification $\alpha_1$, $\alpha_2$ and $\beta_1$, $\beta_2$. Both $\beta_1$ and $\beta_2$ as well as $\alpha_1$ adrenoreceptors are situated primarily on the surface of smooth muscle cells (postsynaptic). In contrast $\alpha_2$-adrenoreceptors have been shown by many workers (Langer, S. Z., Br. J. Pharmac., 1977, 60, 481) to be situated predominantly on the nerve terminals (presynaptic) of noradrenergic nerves. These receptors when stimulated under physiological conditions by the natural transmitter, noradrenaline, inhibit its exocytotic release. Thus, presynaptic adrenoreceptors initiate a negative feed-back loop which regulates transmitter concentration within the synaptic gap.

Agents exist which selectively stimulate (agonists) or block (antagonists) adrenoreceptors of the $\alpha_1$, $\beta_1$ and $\beta_2$ type and some of these have found clinical utility. However, thus far no agent is available with a high degree of selectivity in blocking presynaptic $\alpha_2$-adrenoreceptors. The present invention relates to such a compound.

Selective antagonism of $\alpha_2$-adrenoreceptors would inhibit the negative feedback loop which becomes operational on the release of noradrenaline from the sympathetic nerve endings. Such an inhibition would result in an increase in the synaptic concentration of noradrenaline with a consequent augmentation of the activity of the sympathetic nervous system. Such a drug would be predicted to be of value in conditions which have been postulated to be associated with a deficiency of available noradrenaline at postsynaptic adrenoreceptor sites in the central and/or peripheral nervous system. These conditions include endogenous depression, cardiac failure and conditions associated with excessive bronchoconstriction such as asthma and hay fever. Presynaptic α-adrenoreceptors have also been implicated in humoral processes. For example it has been demonstrated that $\alpha_2$-adrenoreceptor agonists initiate, and antagonists inhibit, human platelet aggregation (Grant, J. A., and Scruton, M. C., Nature, 1979, 277, 659). Thus, a selective presynaptic $\alpha_2$-adrenoreceptor antagonist may be clinically desirable in pathogenic conditions in which platelet aggregation is implicated, for example, migraine.

It has been suggested recently that glucose and lipid metabolism can be controlled either directly or indirectly (via insulin) by an inhibitory mechanism involving $\alpha_2$-adrenoreceptors (Berthelsen & Pettinger, Life Sciences, 1977, 21, 595). $\alpha_2$-Adrenoreceptor antagonists may have a role to play therefore in the control of metabolic disorders such as diabetes and obesity.

Finally, the proximal tubules of the guinea-pig kidney are rich in $\alpha_2$-adrenoreceptors, the activation of which leads to sodium retention (Young & Kuhar, Eur. J. Pharmac., 1980, 67, 493) this suggests that $\alpha_2$-adrenoreceptor antagonists may produce diuresis and hence the compound may have utility as a diuretic.

The invention also includes the use of 2-[2-(1,4-benzodioxanyl)]-2-imidazoline or a non-toxic salt thereof in the treatment of depression and a method of treating depression which comprises administering to humans an antidepressant effective amount of 2-[2-(1,4-benzodioxanyl)]-2-imidazoline or non-toxic salt thereof.

The compound of formula IV may be prepared from a compound of formula V

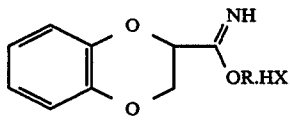
(V)

wherein R is alkyl $C_{1-4}$ and HX is an acid (preferably a pharmaceutically acceptable acid) by treatment with at least one molar equivalent of ethylenediamine. Preferably the reaction is carried out in a polar solvent such as methanol or ethanol. Preferably R is methyl or ethyl, HX is hydrogen chloride and the reaction is carried out in methanol or ethanol respectively.

The compound of formula V may be prepared from a compound of formula VI

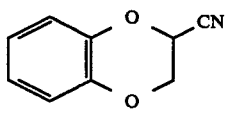
(VI)

by treatment with an alcohol of formula ROH, wherein R is as hereinbefore defined, in the presence of an acid HX where HX is as hereinbefore defined. Most conveniently the alcohol employed is ethanol and HX is hydrogen chloride, the reaction being carried out in anhydrous diethyl ether as solvent.

A particularly convenient method of carrying out the process is to generate the compound of formula V in situ from the compound of formula VI. Thus for example the compound of formula VI dissolved in an alcohol of formula ROH (e.g. methanol or ethanol) is treated with a sodium alkoxide RONa (e.g. sodium methoxide or ethoxide), followed by reaction with hydrogen chloride (conveniently dissolved in an alcohol ROH e.g. methanol or ethanol) and at least one molar equivalent of ethylenediamine.

The following examples illustrate the preparation of the novel compound of the invention and that of the structural isomer previously prepared by the process described in the above mentioned U.S. patent using an improved method of isolation.

In the Examples temperatures are quoted in degrees Celsius. Column chromatography was carried out on alumina (Woelm, neutral alumina, Grade 1). T.l.c. was carried out on alumina (Merck, aluminium oxide 60F$_{254}$ Type E) and silica (Merck, kieselgel 60F$_{254}$). Melting points were determined on a Kofler hot stage apparatus or a Buchi apparatus in glass capillary tubes and are uncorrected. N.M.R. spectra were measured on a Varian Associates T-60 spectrometer at room temperature with tetramethylsilane as internal standard.

H.P.L.C. was carried out using:

Solvent delivery system: Water Associates Ltd. Model-M45.

Mobile phase: 0.1% w/v ammonium acetate in methanol: water (55:45).

Column: Spherisorb 5 μm silica gel packed into 25 cm×0.46 cm i.d. tube.

Detection: UV absorption @ 215 nm (Pye LC3 UV detector).

Injection of samples via Rheodyne 7120 valve and 20 μl loop.

EXAMPLE 1

2-[2-(1,4-Benzodioxanyl)]-2-imidazoline hydrochloride (a)

Ethyl[2-(1,4-benzodioxanyl)]-imidoate hydrochloride

A steady stream of gaseous hydrogen chloride was bubbled through a stirred, cooled solution of 2-cyano-1,4-benzodioxan (88 g) in anhydrous diethyl ether (1 liter) and ethanol (30.8 ml) for 4½ hrs, maintaining the reaction temperature <10° C. After a further 24 hrs at 0-10° the solid was collected, washed with anhydrous diethyl ether and dried to give the desired product as the hydrochloride (110 g; 83%); I.R. $\nu_{max}$ (Nujol) 1670, 1595 cm$^{-1}$.

(b)

2-[2-(1,4-Benzodioxanyl)]-2-imidazoline hydrochloride

A solution of ethylenediamine (16.7 ml) in ethanol (50 ml) was added over 1 hr to a stirred and cooled (0°-10°) solution of ethyl[2-(1,4-benzodioxanyl)]-imidoate hydrochloride (50 g) in ethanol (200 ml). After a further 24 hrs at 0°-10°, any precipitated ethylenediamine dihydrochloride was removed and the volume of the filtrate was reduced (to ~50 ml). More ethylenediamine dihydrochloride was then removed by filtration and the remaining filtrate was treated with an excess of a solution of hydrogen chloride in diethyl ether. Addition of a further amount of diethyl ether gave a precipitate of the crude product (44 g) which was recrystallised from isopropanol to give a white crystalline product (34 g; 68%), m.p. 207°-208°; I.R. $\nu_{max}$ (Nujol) 1625, 1590 cm$^{-1}$; M.S. m/e 204(M+), 174(100%); N.M.R.

τ(DMSO) −1.4(2H, s, NH and HCl-exchanged D$_2$O), 3.05 (4H, s, aryl-H), 4.4(1H, t, J 4 Hz, —OCH—), 5.4(2H, d, J 4 Hz, —OCH$_2$—), 6.1(4H, s, N—CH$_2$CH$_2$—N);

Found: C, 54.98; H, 5.67; N, 11.68; C$_{11}$H$_{12}$N$_2$O$_2$.HCl requires C, 54.89; H, 5.44, N, 11.64%.

The following t.l.c. systems showed the product to be homogeneous:

| Alumina | Chloroform | R$_f$ ~ 0.5 |
|---|---|---|
| Silica | Chloroform:Methanol 4:1 | R$_f$ ~ 0.1 |
| Silica | Chloroform:Methanol 1:1 | R$_f$ ~ 0.2 |
| Silica | Chloroform:Methanol 1:4 | R$_f$ ~ 0.3 |

H.P.L.C. analysis indicated the sample to be ≧99%. 2-[2-(2-methyl-1,3-benzodioxyl)]-2-imidazoline and N-(2-aminoethyl)-1,4-benzodioxan-2-carboxamide could not be detected (both <0.1%) in this product.

EXAMPLE 2

2-[2-(2-methyl-1,3-benzodioxyl)]-2-imidazoline hydrochloride

A mixture of 1,4-benzodioxan-2-carboxylic acid (39 g) and ethylenediamine (69 ml) was heated under reflux for 18 hrs. A quantity of distillate (15 ml) was collected to remove water and a further quantity of ethylenediamine (15 ml) was added. The mixture was heated under reflux for a further 8 hrs and then concentrated by distillation. The residue was fractionally distilled to give an almost colourless product (13.2 g) b.p. 156°-160°/1 mm Hg. [T.l.c. indicated that the major component of the reaction, together with catechol, was formed during this distillation step. H.P.L.C. analysis indicated the following compounds to be present: 2-[2-(2-methyl-1,3-benzodioxyl)]-2-imidazoline~49%; catechol~24%; N-(2-aminoethyl)-1,4-benzodioxan-2-carboxamide~11%; 2-[2-(1,4-benzodioxanyl)]-2-imidazoline~4%].

Catechol was removed by partitioning the distillate between ethyl acetate and 2N aqueous sodium hydroxide solution and the organic phase was dried and evaporated to leave a semisolid which was dissolved in ethanol and treated with ethanolic hydrogen chloride. Dilution with diethyl ether gave a semisolid which yielded a solid on trituration with acetonitrile. Recrystallisation from isopropanol gave a slightly impure sample of the product as its hydrochloride salt. An improved procedure of purification was to filter a solution of the distillate (in methylene chloride: light petroleum 40-60) through an alumina column prior to hydrochloride salt formation; this removed the catechol contaminant. The purified salt was finally recrystallised from isopropanol to give a colourless solid (0.9 g; 2%) m.p. ~245° (dec.); I.R. ν$_{max}$(Nujol) 1620, 1590 cm$^{-1}$; MS m/e 204(M+), 161(100%); N.M.R. τ(DMSO)−1.2(2H, s, NH and HCl—exchanged in D$_2$O), 3.0(4H, s, aryl-H), 6.05(4H, s, N—CH$_2$CH$_2$—N), 7.85(3H, s, CH$_3$);

Found: C, 54.75; H, 5.51; N, 11.53; C$_{11}$H$_{12}$N$_2$O$_2$.HCl requires C, 54.89; H, 5.44; N, 11.64%.

The following t.l.c. system showed the product to be homogeneous:

| Alumina | Chloroform | R$_f$ ~0.6 |
|---|---|---|
| Silica | Chloroform:Methanol 4:1 | R$_f$ ~0.3 |
| Silica | Chloroform:Methanol 1:1 | R$_f$ ~0.4 |
| Silica | Chloroform:Methanol 1:4 | R$_f$ ~0.5 |

H.P.L.C. analysis of the sample indicated the presence of N-(2-aminoethyl)-1,4-benzodioxan-2-carboxamide (0.6%). 2-[2-(1,4-Benzodioxanyl)]-2-imidazoline could not be detected (<0.3%) in this product.

EXAMPLE 3

2-[2-(1,4-Benzodioxanyl)]-2-imidazoline hydrochloride

A solution of sodium methoxide (1.45 g) in methanol (20 ml) was added over one minute to a stirred solution of 2-cyano-1,4-benzodioxan (145 g) in methanol (870 ml) at room temperature. After stirring for a further 4 hrs at room temperature the solution was cooled and ethylenediamine (64.7 g) was added dropwise at 5°. A solution of hydrogen chloride in methanol (134 g of solution containing 34.8 g hydrogen chloride) was then added to the stirred solution over 2 hrs at 5°. After a further 20 hrs at 0°-10° precipitated ethylenediamine dihydrochloride was removed by filtration and the filtrate was reduced to 300 g in vacuo at 40°. Further ethylenediamine dihydrochloride was removed and the remaining filtrate evaporated in vacuo at 40° to dryness. The solid residue (225 g) was stirred with dichloromethane (1.1 liters) and dry hydrogen chloride was bubbled through at 5°-10° till in slight excess. The crude product was then removed by filtration (172 g) and combined with a 2nd crop (24 g) obtained by concentration of the filtrate in vacuo at 40°. Crystallisation of these two crops from ethanol with hot filtration and concentration of the filtrate in vacuo to 384 g gave an off white crystalline product (175.5 g, 81%), m.p. 207°-208°. Product identical to that of Example 1 (N.M.R., M.S., I.R.).

Reverse order of addition of the ethylenediamine and hydrogen chloride in methanol affords a similar yield.

The following is a comparison of some of the different physical characteristics of the two compounds of Examples 1 and 2, both of which were hydrochloride salts recrystallised from isopropanol:

|  |  |  |  | Example | |
|---|---|---|---|---|---|
|  |  |  |  | 1 | 2 |
| melting point °C. |  |  |  | 207–208 | ~245 (dec) |
| t.l.c. | alumina | chloroform | R$_f$ | 0.5 | 0.6 |
|  | silica | chloroform:methanol 4:1 | R$_f$ | 0.1 | 0.3 |
|  | silica | chloroform:methanol 1:1 | R$_f$ | 0.2 | 0.4 |
| t.l.c. | alumina | chloroform:methanol 1:4 | R$_f$ | 0.3 | 0.5 |

With respect to the N.M.R. data as given above, that for Example 1 shows two distinct multiplets in the region τ4.4 (1 proton) and τ5.4 (2 protons) characteristic of the dioxan ring of the formula IV. (The above mentioned cyano-compound of formula VI shows similar multiplets in the region τ5.1 (1 proton) and τ5.7 (2 protons)). In contrast the spectrum for the compound of Example 2 shows a 3 proton singlet at τ7.85 characteristic of the methyl group of the formula III and the lack of any signals in the region τ4.0 to 6.0 indicating the absence of a dioxan ring.

The pharmacological activity of the compound of the present invention, as its hydrochloride, (Example 1) has been determined. For convenience this compound is denoted in the following Tables as "A" whilst the isomeric compound (Example 2) is denoted as "B".

1. Pre- and postsynaptic α-adrenoreceptor antagonism in isolated tissue experiments Initial biological evaluation of presynaptic $\alpha_2$-adrenoreceptor antagonism was assessed by determining $pA_2$ values against the inhibitory effects of clonidine, a well known presynaptic α-adrenoreceptor agonist, on the rat vas deferens stimulated at a frequency of 0.1 Hz according to the method of Doxey, J. C., Smith, C. F. C., and Walker, J. M., Br. J. Pharmac., 1977, 60, 91.

This in vitro model is particularly useful as an initial screen for studying presynaptic activity in isolation since the physiological nature of the vas deferens tissue is such that the post synaptic receptors located therein are particularly inaccessible to exogenous agents. In consequence an alternative tissue, the rat anococcygeus muscle is used to establish postsynaptic α-adrenoreceptor activity. Antagonism of noradrenaline contractions is used to determine $pA_2$ values at postsynaptic α-adrenoreceptors. The ratio of presynaptic α-adrenoreceptor antagonism (versus clonidine on the rat vas deferens) to postsynaptic α-adrenoreceptor antagonism (versus noradrenaline contractions on the rat anococcygeus muscle) is used to assess adrenoreceptor selectivity. The $pA_2$ values for compounds A and B are shown in Table 1. Table 1 also includes the results for four standard drugs: (i) the non-selective α-adrenoreceptor antagonist, phentolamine, (ii) the selective presynaptic antagonist, yohimbine, (iii) the highly selective postsynaptic antagonist, prazosin and (iv) the antidepressant, mianserin which shows non-selective pre- and postsynaptic adrenoreceptor antagonist properties as part of its pharmacological profile.

TABLE 1

| Compound | Presynaptic antagonism $pA_2$ vs Clonidine (vas deferens) | Postsynaptic antagonism $pA_2$ vs Noradrenaline (anococcygeus) | Pre/post synaptic ratio |
|---|---|---|---|
| A | 8.5 | 6.2 | 225 |
| B | 6.2 | <4.4 | >67 |
| Phentolamine | 8.4 | 7.7 | 4.8 |
| Yohimbine | 8.2 | 6.4 | 60 |
| Prazosin | <6.6 | 8.2 | <0.03 |
| Mianserin | 7.3 | 6.6 | 5.0 |

("<" means inactive at a concentration which would have given the $pA_2$ indicated).

The results are the mean of a minimum of 5 experiments.

It can be seen in Table 1 that of the compounds studied, compound A was the most potent presynaptic α-adrenoreceptor antagonist and was moreover the most selective for presynaptic sites. In particular compound A was two hundred times more potent than compound B as a presynaptic antagonist.

2. Presynaptic α-adrenoreceptor antagonism in the pithed rat (1) Rat vas deferens-intravenous activity This test model extends the evaluation of presynaptic α-adrenoreceptor antagonism versus clonidine on the rat vas deferens to the in vivo situation. Blood pressure and stimulation induced contractions of the vas deferens were monitored in pithed rats using the method of Brown, J., Doxey, J. C., Handley, S. and Virdee, N., Recent Advances in the Pharmacology of Adrenoceptors, Elsevier North Holland, 1978. Clonidine (100 μg/kg, i.v.) causes a prolonged pressor response and a prolonged inhibition of vas deferens contractions. The test drugs were injected intravenously in a cumulative dosing schedule and their abilities to reverse the inhibition of hypogastric nerve stimulation reflected their presynaptic antagonism. Table 2 shows the doses of antagonists which caused a 50% reversal of the inhibition of hypogastric nerve stimulation.

TABLE 2

Relative antagonist potencies at presynaptic α-adrenoreceptors in the pithed rat.

| Compound | i.v. dose of antagonist causing 50% reversl of clonidine block on vas deferens mg/kg |
|---|---|
| A | 0.009 |
| B | 5.60 |
| Yohimbine HCl | 0.86 |
| Mianserin HCl | >4.4 |
| Phentolamine mesylate | 0.12 |

The results are the mean of a minimum of 4 rats.

Under the chosen experimental conditions all of the compounds studied, with the exception of mianserin and compound B produced a complete reversal of the inhibitory effects of clonidine on hypogastric nerve stimulation. The maximum reversals seen with mianserin and compound B were 36% and 66% respectively at cumulative intravenous doses of 4.4 mg/kg and 14.4 mg/kg respectively. It can be seen from Table 2 that compound A is clearly the most potent presynaptic α-adrenoreceptor antagonist of those studied.

(2) Rat vas deferens—oral activity

The previous test situation (2.1) was modified to establish the oral activity of compound A.

Groups of 5 rats were dosed orally with either saline (1.0 ml/100 g body weight) or compound A (1.0 and 5.0 mg/kg). Thirty minutes after oral administration, the rats were pithed so as to allow electrically-induced contractions of the vas deferens to be studied in situ. Dose-response curves to the presynaptic agonist properties of clonidine were constructed 75 minutes after saline or compound A administration.

Orally administered compound A produced a dose-dependent competitive antagonism of the presynaptic action of clonidine. The cumulative doses of clonidine which inhibited the twitch response of the vas deferens by 50% in rats given saline, 1.0 and 5.0 mg/kg compound A were 6.6, 20.5 and 93.0 μg/kg, i.v. respectively. No inhibition of the clonidine postsynaptic effects (blood pressure increases) occurred after 1.0 mg/kg compound A although some antagonism was observed at 5.0 mg/kg.

TABLE

Presynaptic α-adrenoreceptor antagonism following oral administration

| Treatment | Dose of Clonidine of vas deferens μg/kg (i.v.) |
|---|---|
| Saline | 6.6 |
| A 1 mg/kg (p.o.) | 20.5 |
| A 5 mg/kg (p.o.) | 93.0 |

3. Rat anococcygeus muscle-intravenous activity

In contrast to the rat vas deferens, both the pre- and postsynaptic adrenoreceptors of the rat anococcygeus muscle are readily accessible to exogenously applied agents and therefore this test can be used to distinguish selective presynaptic α-adrenoreceptor antagonists from non-selective agents. Contractions of the rat anococcygeus muscle induced by low frequency (1 Hz) electrical stimulation of spinal sympathetic outflow are inhibited by low doses of clonidine. Only selective presynaptic α-adrenoreceptor antagonists will reverse the inhibitory effects of clonidine. Thus yohimbine (0.3–1.0 mg/kg, i.v.) fully reversed the inhibitory action of clonidine on the anococcygeus muscle. Further studies were carried out using this model except that guanabenz acetate (30 μg/kg, i.v.), a more selective presynaptic α-adrenoreceptor agonist than clonidine was used. It can be seen in Table 4 that compound A was approximately 14 times more potent than yohimbine as a presynaptic α-adrenoreceptor antagonist. In this model phentolamine was devoid of presynaptic α-adrenoreceptor antagonist activity at a cumulative i.v. dose of 1.4 mg/kg. On the basis of these results compound A is the most potent presynaptic α-adrenoreceptor antagonist studied and in contrast to phentolamine is very selective for presynaptic α-adrenoreceptors.

TABLE 4

Presynaptic α-adrenoreceptor antagonism in the anococcygeus muscle of the pithed rat.

| Compound | Intravenous dose of antagonist causing 50% reversal of guanabenz block of anococcygeus muscle mg/kg |
|---|---|
| A | 0.021 |
| Yohimbine HCl | 0.280 |
| Phentolamine mesylate | >1.4 |

4. Effect on blood pressure and heart rate of conscious DOCA hypertensive rats

The blood pressure and heart rate effects of 1.0, 5.0 and 20.0 mg/kg, compound A were compared to the same doses of compound B and phentolamine given orally to DOCA hypertensive rats. Results are given in Table 5 in terms of peak percentage fall in B.P.

TABLE 5

| Drug | 1.0 | 5.0 | 20.0 mg/kg |
|---|---|---|---|
| A | −4 | −28 | −39 |
| B | −15 | −25 | −14 |
| Phentolamine | −16 | −24 | −41 |

Compound A (5.0 and 20.0 mg/kg) produced dose-related falls in mean arterial blood pressure. The blood pressure lowering effects of these two doses of compound A were similar to responses with the same doses of phentolamine.

At the 1.0 mg/kg dose level, compound A did not significantly alter blood pressure. Thus, an oral dose of compound A which selectively inhibits presynaptic α-adrenoreceptors (See section 2.2) does not possess antihypertensive activity. In contrast, phentolamine (1.0 mg/kg) reduced blood pressure in DOCA rats. Phentolamine has been shown both in vitro and in vivo experiments not to possess significant selectivity towards either pre- or postsynaptic α-adrenoreceptors.

Heart rate was reflexly elevated in response to the blood pressure reduction observed with 20 mg/kg phentolamine. Heart rate was not greatly affected by the two smaller doses of phentolamine. No significant effect on heart rate was noted with the three doses of compound A used in this study.

In contrast to compound A, compound B induced a significant antihypertensive effect at the lowest dose studied (1 mg/kg, p.o.). The falls in blood pressure produced by compound B were not dose-related; the maximum hypotensive effect following 20 mg/kg, p.o. compound B being less than that produced by 5 mg/kg, p.o. compound B. It is assumed that the mechanisms responsible for the hypotensive activity of compounds A and B are different and the lack of a dose-related effect with the latter could be due to postsynaptic α-adrenoreceptor agonist activity which was detected in a separate experiment where pressor responses in the pithed rat were seen on intravenous administrtion of compound B at doses of 1–10 mg/kg.

5. Effect in the CNS

Antagonism of clonidine-induced hypothermia

In a recent study Von Voigtlander et al Neuropharmac., 178, 17, 375 demonstrated that several antidepressants and α-adrenoreceptor antagonists inhibited clonidine-induced hypothermia following chronic but not acute administration of these agents. These results were in keeping with the delayed onset seen with antidepressants in the clinic.

The ability of both compound A and compound B to antagonise clonidine-induced hypothermia was studied in mice. A statistically significant dose-related reversal of clonidine-induced hypothermia was seen following intravenous doses of 0.1–1.0 mg/kg compound A. Compound B produced a partial reversal of clonidine-induced hypothermia over the dose range 1–10 mg/kg, i.v. The reversal seen with compound B however, was not significantly different from animals treated with vehicle. As a dose of 30 mg/kg i.v., compound B potentiated the clonidine-induced hypothermia.

The pharmaceutical compositions may be in a form suitable for oral, rectal or parenteral administration. Such oral compositions may be in the form of capsules, tablets, granules or liquid preparations such as elixirs, syrups or suspensions.

Tablets contain a compound of formula IV or a non-toxic salt thereof in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or Kaolin in a hard gelatine capsule.

Compositions for parenteral administration may be in the form of sterile injectable preparations such as solutions or suspensions in for example water, saline or 1,3-butane diol.

For the purposes of convenience and accuracy of dosing the compositions are advantageously employed in a unit dosage form. For oral administration the unit dosage form contains from 1 to 200 mg, preferable 10 to 50 mg of the compound of Formula IV or a non-toxic salt thereof. Parenteral unit dosage forms contains from 0.1 to 10 mg of the compound of Formula IV or a non-toxic salt thereof per 1 ml of the preparation.

The invention is further illustrated by the following Examples of compositions in which all parts are by weight.

EXAMPLE 1

A mixture of one part 2-[2-(1,4-benzodioxanyl)]-2-imidazoline hydrochloride and four parts microcrystalline cellulose together with 1% of magnesium stearate is compressed into tablets. Conveniently the tablets are of such a size as to contain 10, 25 or 50 mg of the active ingredient.

EXAMPLE II

A mixture of one part 2-[2-(1,4-benzodioxanyl)]-2-imidazoline hydrochloride and four parts spray dried lactose together with 1% magnesium stearate is filled into hard gelatin capsules. The capsules may conveniently contain 10, 25 or 50 mg of the active ingredient.

We claim:

1. A pharmaceutical composition in oral unit dosage form for selective presynaptic $\alpha_2$-adrenoreceptor antagonist use comprising from 10 to 50 mg of 2-[2-(1,4-benzodioxanyl)]-2-imidazoline or non-toxic salt thereof, together with a pharmaceutically acceptable diluent or carrier.

2. A pharmaceutical composition in parenteral unit dosage form for selective presynaptic $\alpha_2$-adrenoreceptor antagonist use comprising from 0.1 to 10 mg per 1 ml of the composition of 2-[2-(1,4-benzodioxanyl)]-2-imidazoline or non-toxic salt thereof, together with a pharmaceutically acceptable diluent or carrier.

3. A method of treating depression which comprises administering to a human an antidepressant effective amount of 2-[2-(1,4-benzodioxanyl)]-2-imidazoline or a non-toxic salt thereof.

4. A method of producing selective presynaptic $\alpha_2$-adrenoreceptor antagonist activity in a human host which comprises administering to a human requiring such activity an effective amount of 2-[2-(1,4-benzodioxanyl)]-2-imidazoline or a non-toxic salt thereof.

* * * * *